(12) United States Patent
Ferrari et al.

(10) Patent No.: US 7,994,352 B2
(45) Date of Patent: Aug. 9, 2011

(54) PROCESS FOR PREPARING 3A(β)-7A(β)-DIHYDROXY-6A(β)-ALKYL-5β-CHOLANIC ACID

(75) Inventors: Massimo Ferrari, Cenate Sotto (IT); Roberto Pellicciari, Perugia (IT)

(73) Assignee: Intercept Pharmaceuticals, Inc., New York, NY (US)

(*) Notice: Subject to any disclaimer, the term of this patent is extended or adjusted under 35 U.S.C. 154(b) by 929 days.

(21) Appl. No.: 11/914,559

(22) PCT Filed: May 19, 2006

(86) PCT No.: PCT/EP2006/062446
§ 371 (c)(1),
(2), (4) Date: Nov. 16, 2007

(87) PCT Pub. No.: WO2006/122977
PCT Pub. Date: Nov. 23, 2006

(65) Prior Publication Data
US 2008/0214515 A1     Sep. 4, 2008

(30) Foreign Application Priority Data
May 19, 2005  (IT) .............................. MI2005A0912

(51) Int. Cl.
*C07J 9/00* (2006.01)
(52) U.S. Cl. .................................................... 552/551
(58) Field of Classification Search .................. 552/551; 514/182
See application file for complete search history.

(56) References Cited

U.S. PATENT DOCUMENTS

| | | | |
|---|---|---|---|
| 4,892,868 A | 1/1990 | Castagnola et al. | |
| 4,921,848 A | 5/1990 | Frigerio et al. | |
| 5,061,701 A | 10/1991 | Pellicciari et al. | |
| 5,128,481 A | 7/1992 | Oda et al. | |
| 5,175,320 A | 12/1992 | Pellicciari et al. | |
| 6,200,998 B1 | 3/2001 | Sahoo et al. | |
| 6,559,188 B1 | 5/2003 | Gatlin et al. | |
| 6,639,078 B1 | 10/2003 | Haffner et al. | |
| 6,777,446 B2 | 8/2004 | Houze et al. | |
| 6,906,057 B1 | 6/2005 | Forman et al. | |
| 6,984,650 B2 | 1/2006 | Haffner et al. | |
| 6,987,121 B2 | 1/2006 | Kliewer et al. | |
| 7,138,390 B2 | 11/2006 | Pellicciari | |
| 2002/0094977 A1 | 7/2002 | Robl et al. | |
| 2002/0120137 A1 | 8/2002 | Houze et al. | |
| 2002/0132223 A1 | 9/2002 | Forman et al. | |
| 2003/0130296 A1 | 7/2003 | Bauer et al. | |

FOREIGN PATENT DOCUMENTS

| EP | 0101554 A2 | 2/1984 |
|---|---|---|
| EP | 0124068 A1 | 11/1984 |
| EP | 0135782 A2 | 4/1985 |
| EP | 0186023 A2 | 7/1986 |
| EP | 312867 * | 4/1989 |
| EP | 0393493 A2 | 10/1990 |
| EP | 1137940 A1 | 10/2001 |
| EP | 1140079 A1 | 10/2001 |
| EP | 1165135 A1 | 1/2002 |
| EP | 1185277 A1 | 3/2002 |
| EP | 1378749 A1 | 1/2004 |
| EP | 1473042 A1 | 11/2004 |
| EP | 1536812 A2 | 6/2005 |
| EP | 1568706 | 8/2005 |
| EP | 1947108 A1 | 7/2008 |
| WO | WO-9728149 A1 | 8/1997 |
| WO | WO-9736579 A1 | 10/1997 |
| WO | WO-9802159 A1 | 1/1998 |
| WO | WO-9938845 A1 | 8/1999 |
| WO | WO-0025134 A1 | 5/2000 |
| WO | WO-0037077 A1 | 6/2000 |
| WO | WO-0040965 A1 | 7/2000 |
| WO | WO-0057915 A1 | 10/2000 |
| WO | WO-0076523 A1 | 12/2000 |
| WO | WO-0130343 A1 | 5/2001 |
| WO | WO-9731907 A | 6/2001 |

(Continued)

OTHER PUBLICATIONS

Mangelsdorf, David J. et al; "The RXR Heterodimers and Orphan Receptors"; Cell, vol. 83; 841-850; Dec. 15, 1995.
Forman, Barry M. et al; "Identification of a Nuclear Receptor That Is Activated by Farnesol Metabolites"; Cell; vol. 81; 687-693; Jun. 2, 1995.
Pellicciari, Roberto et al.; "Bile Acid Derivatives as Ligands of the Farnesoid X Receptor. Synthesis, Evaluation and Structure-Activity Relationship of a Series of Body and Side Chain Modified Analogues of Chenodeoxycholic Acid"; Journal of Med. Chem., 47(18), 4559-4569 CODEN: JMCMAR 2004.
Pellicciari, Roberto et al; "6.Alpha.-Ethyl-Chenodeoxycholic Acid (6-ECDCA), a Potent and Selective FXR Agonist Endowed with Anticholestatic Activity"; Journal of Med. Chem., 45(17), 3569-3572 CODEN: JMCMAR 2002.

(Continued)

*Primary Examiner* — Barbara P Badio
(74) *Attorney, Agent, or Firm* — Mintz, Levin, Cohn, Ferris, Glovsky, and Popeo, P.C.; Ivor R. Elrifi, Esq.; Jennifer L. Loebach

(57) ABSTRACT

Process for preparing 3α-7α(β)-dihydroxy-6α(β)-alkyl-5β-cholanic acid (I) in which R is a linear or branched $C_1$-$C_5$ alkyl and the relative intermediates 3α-hydroxy-6β-alkyl-7-keto-5β-cholanic (VIII) and 3α-hydroxy-6α-alkyl-7-keto-5β-cholanic (IX).

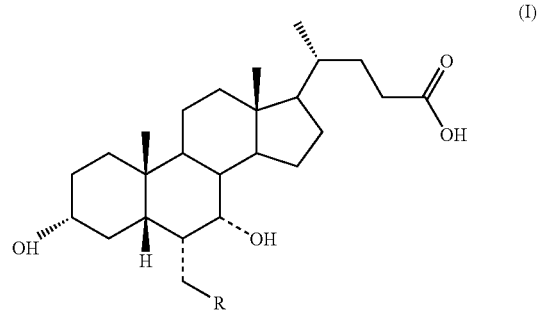

39 Claims, No Drawings

FOREIGN PATENT DOCUMENTS

| WO | WO-0220463 A2 | 3/2002 |
|---|---|---|
| WO | WO-02064125 A2 | 8/2002 |
| WO | WO 02/072598 | 9/2002 |
| WO | WO-03015771 A1 | 2/2003 |
| WO | WO-03015777 A1 | 2/2003 |
| WO | WO-03016280 A1 | 2/2003 |
| WO | WO-03016288 A1 | 2/2003 |
| WO | WO-03030612 A2 | 4/2003 |
| WO | WO-03043581 A2 | 5/2003 |
| WO | WO 03/080803 * | 10/2003 |
| WO | WO-03086303 A2 | 10/2003 |
| WO | WO-03090745 A1 | 11/2003 |
| WO | WO-200400752 A2 | 1/2004 |
| WO | WO-2004048349 A1 | 6/2004 |
| WO | WO-2005032549 A1 | 4/2005 |
| WO | WO-2005082925 A2 | 9/2005 |
| WO | WO-2005089316 A2 | 9/2005 |
| WO | WO-2006122977 A2 | 11/2006 |
| WO | WO-2008002573 A2 | 1/2008 |
| WO | WO-2008091540 A2 | 7/2008 |
| WO | WO-2010/059853 A1 | 5/2010 |

OTHER PUBLICATIONS

Aldini et al., "Relationship between structure and intestinal absorption of bile acids with a steroid or side-chain modification", *Steroids*, 61(10):590-597 (1996).

Bishop-Bailey et al., "Expression and activation of the farnesoid X receptor in the vasculature", *Proc. Natl. Acad. Sci. U.S.A.*, 101(10):3668-3673 (2004).

Clerici et al., "Effect of Intraduodenal Administration of 23-Methyl-UDCA Diastereoisomers on Bile Flow in Hamsters", *Dig. Dis. Sci.*, 37(5):791-798 (1992).

Fiorucci et al., "The Nuclear Receptor SHP Mediates Inhibition of Hepaptic Stellate Cells by FXR and Protects Against Liver Fibrosis", *Gastroenterology*, 127:1497-1512 (2004).

Fukuchi et al., "5β-Cholane activators of the farnesol X receptor", *J. Steroid Biochem. Mol. Biol.*, 94(4):311-318 (2005).

Haslewood et al., "Specificity and some characteristics of a 7.alpha.-hydroxysteroid dehydrogenase from *E. coli*", Database accession No. 1978:419015, 1998.

Honorio et al., "Hologram QSAR Studies on Farnesoid X Receptor Activators", *Lett. Drug Des. Dis.*, 3(4):261-267 (2006).

Kihira et al., "Synthesis of sulfonate analogs of bile acids",*Steroids*, 57(4):193-198 (1992).

Kim et al., "Hypocholesterolemic Effect of Bile Acid Sulfonate Analogs in Hamsters", *Biol.Pharm. Bulletin*, 24(3):218-220 (2001).

Kliewer et al., "Peroxisome Proliferator-Activated Receptors: From Genes to Physiology", *Endo J.*, 56:239-263 (2001).

Mi et al., "Structural Basis for Bile Acid Binding and Activation of the Nuclear Receptor FXR", *Mol. Cell*, 11:1093-1100 (2003).

Mikami et al., "Effect of some sulfonate analogues of ursodeoxycholic acid on biliary lipid secretion in the rat", *J. Lipid Res.*, 37(6)1181-1188 (1996).

Miki et al., "Sulfonate analogues of chenodeoxycholic acid: metabolism of sodium 3α, 7α-dihydroxy-25-homo-5β-cholane-25-sulfonate and sodium 3α, 7α-dihydroxy-24-nor-5β-cholane-23-sulfonate in the hamster", *J. Lipid Res.*, 33(11):1629-1637 (1992).

Nesto et al., "Thiazolidinedione Use, Fluid Retention, and Congestive Heart Failure", *Diabetes Care*, 27(1):256-263 (2004).

Pellicciari et al.,"Nongenomic Actions of Bile Acids. Synthesis and Preliminary Characterization of 23- and 6,23-Alkyl-Substituted Bile Acid Derivatives as Selective Modulators for the G-Protein Coupled Receptor TGR5", *J. Med. Chem.*, 50:4265-4268 (2007).

Raskin et al., "A Randomized Trial of Rosiglitazone Therapy in Patients With Inadequately Controlled Insulin-Treated Type 2 Diabetes", *Diabetes Care*, 24(7):1226-1232 (2001).

Roda et al., "23-Methyl-3α.,7β-dihydroxy-5β-cholan-24-oic Acid: Dose-Response Study of Biliary Secretion in Rat", *Hepatol.*, 8(6):1571-1576 (1988).

Roda et al., "Bile acids with a cyclopropyl-containing side chain. IV. Physicochemical and biological properties of the four diastereoisomers of 3α,7β-dihydroxy-22,23-methylene-5β-cholan-24-oic acid", *J. Lipid Res.*, 28(12):1384-1397 (1987).

Rubin et al., "Combination Therapy With Pioglitazone and Insulin in Patients With Type 2 Diabetes", *Diabetes*, 48(Suppl. 1):A110 (1999) (Abstract Only).

Sato et al., "Novel Potent and Selective Bile Acid Derivatives as TGR5 Agonists: Biological Screening, Structure-Activity Relationships, and Molecular Modeling Studies", *J. Med. Chem.*, 51(6):1831-1841 (2008).

Schmider et al., "Evidence for an additional sinusoidal bile salt transport system", Database accession No. 2000:260886, Feb. 16, 2009.

Souillac et al., "Characterization of Delivery Systems, Differential Scanning Calorimetry", in *Encyclopedia of Controlled Drug Delivery*, John Wiley & Sons, pp. 212-227 (1999).

Stenner et al., "The effect of ursodeoxycholic acid on fibrosis markers in alcoholic liver disease", *Flak Symposium*, pp. 229-235 (2002).

Vippagunta et al., "Crystalline solids", *Adv. Drug Del. Rev.*, 48:3-26 (2001).

Willson et al., "The PPARs: From Orphan Receptors to Drug Discovery", *J. Med. Chem.*, 43(4):527-550 (2000).

\* cited by examiner

PROCESS FOR PREPARING 3A(β)-7A(β)-DIHYDROXY-6A(β)-ALKYL-5β-CHOLANIC ACID

RELATED APPLICATIONS

This patent application is a national stage application, filed under 35 U.S.C. §371, of International Application No. PCT/EP2006/062446, filed May 19, 2006, which claims the benefit of and priority to Italian Application No. MI2005A000912, filed May 19, 2005.

FIELD OF THE INVENTION

The present invention concerns a process for the preparation of 3α-7α(β)-dihydroxy-6α(β)-alkyl-5β-cholanic acids.

STATE OF THE ART

Farnesoid X receptors (FXR) are initially orphan nuclear receptors, identified for the first time from a cDNA library of rat liver (B. M Forman et al., *Cell*. 81:687-693 (1995)), they are members of the family of nuclear receptors of ligand-activated transcription factors, including the receptors of steroid, retinoid and thyroid hormones (D. J. Mangelsdorf, et al, *Cell*. 88:841-850 (1995)).

Several bile acids of a natural type bind together and activate FXR in physiological concentrations as described in WO00/37077 and in particular chenodeoxycholic, deoxycholic, litocholic acids and the relative conjugates with taurine and glycine.

It is also believed that FXR are involved in the regulation of the homeostasis of bile acids and of cholesterol.

WO02/072598 describes 3-α,7-α-dihydroxy-6α-alkyl-(allyl)-5β-cholanic acids with general formula (A)

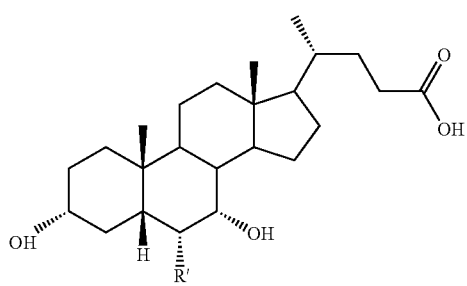

in which R' is ethyl, propyl or allyl which are also agonists of Farnesoid X receptors.

In particular the compound with formula (I) in which R'=ethyl is two magnitude order more powerful than chenodeoxycholic acid, the most powerful natural FXR agonist The compounds with general formula (A), used in particular to increase HDL cholesterol, to lower triglycerides for the prevention and treatment of hepatic diseases of cholestatic origin, are prepared with a process comprising the following stages:

i) reacting 3-α-hydroxy-7-keto-5β-cholanic acid of formula (II)

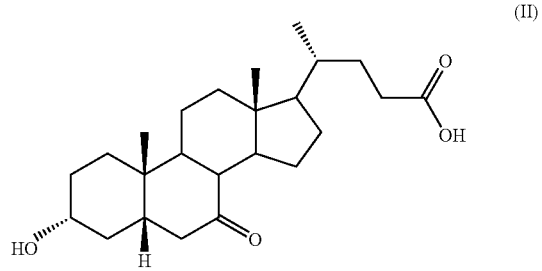

with dihydro pyrane to obtain the corresponding 3-α-tetrahydropyranyloxy-7-keto-5β-cholanic acid of formula (B)

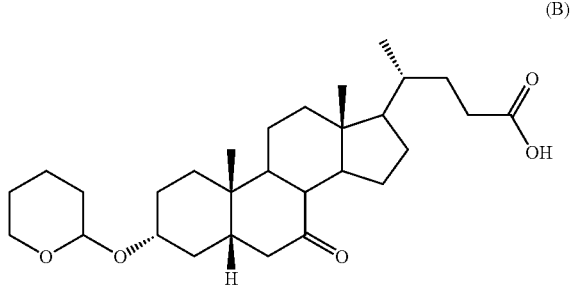

ii) reacting the compound (B) with an alkyl bromide with formula R'Br in which R' has the meanings indicated above, to obtain the compound (C)

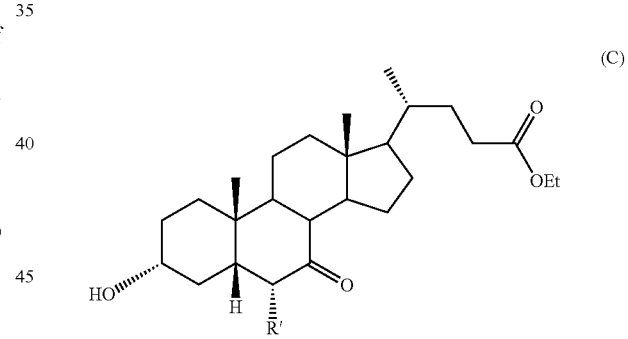

iii) reducing the compound (C) with sodium borohydride to give (D),

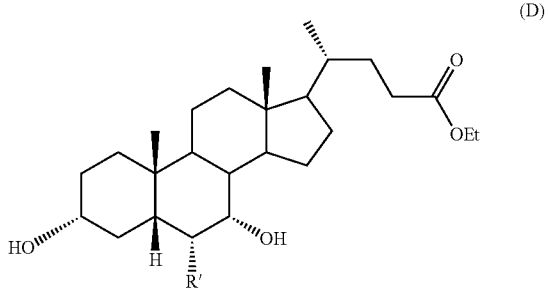

iv) hydrolysing (D) to give the compounds (A).

Even though this process comprises only few stages, it presents a series of drawbacks.

Firstly, in all stages the reaction products are purified on a chromatographic column, namely a very expensive separation method that cannot be realised on an industrial scale.

Moreover the reaction yield in stage (ii) is extremely low (12-13%), with a considerable decrease in the global yield, which is lower than 3.5%.

Moreover, still in this stage, hexamethylenphosphonamide is used as a reactant, which is a known cancerogenic agent

SUMMARY OF THE INVENTION

The Applicant has now found a process which makes it possible to obtain both compounds with general formula (I)

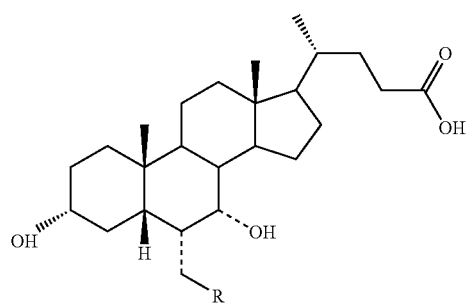

(I)

in which the dashed bond (—) in position 6 and 7 indicates that the substituent may be in position α or β chosen in the class consisting of:

i) 3-α,7-α-dihydroxy-6-α-alkyl-5β-cholanic acid with general formula (IA)

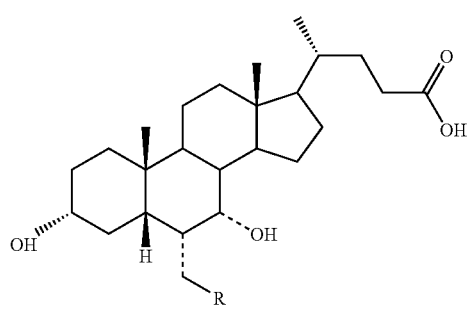

(IA)

ii) 3-α,7-α-dihydroxy-6-β-alkyl-5β-cholanic acid with general formula (IB)

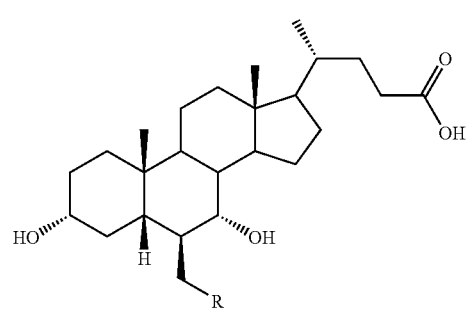

(IB)

iii) 3-α,7-β-dihydroxy-6-α-alkyl-5β-cholanic acid with general formula (IC)

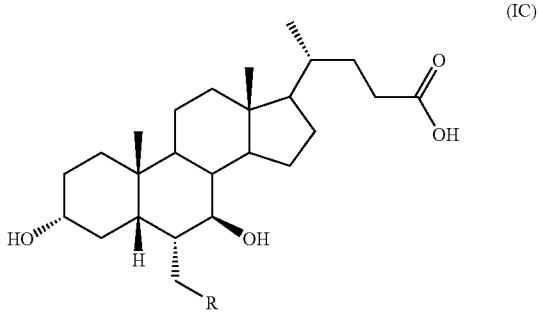

(IC)

in which R is a linear or branched $C_1$-$C_5$ alkyl, comprising the following stages a) esterifying 3α-hydroxy-7-keto-5β-cholanic acid (II)

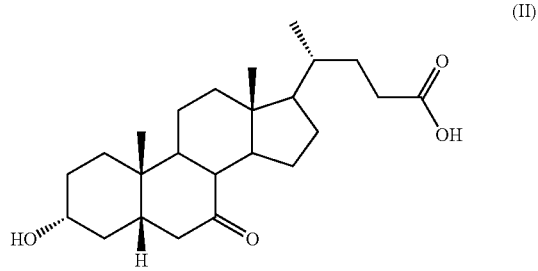

(II)

in methanol in an acidic environment to obtain methyl 3α-hydroxy-7-keto-5β-cholanate (III),

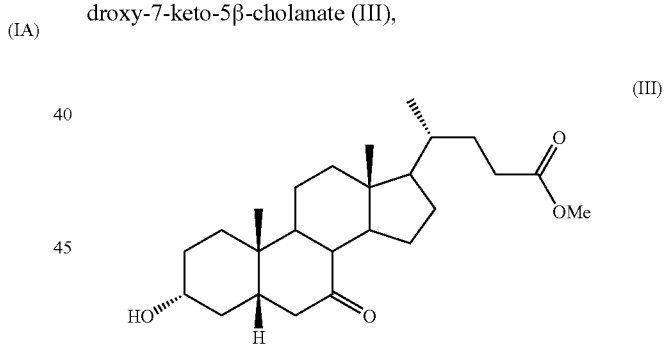

(III)

b) Silylating methyl 3α-hydroxy-7-keto-5β-cholanate (III) with trimethylchlorosilane to obtain the corresponding 3-α-trimethylsiloxy-7-keto-5β-cholanate (IV),

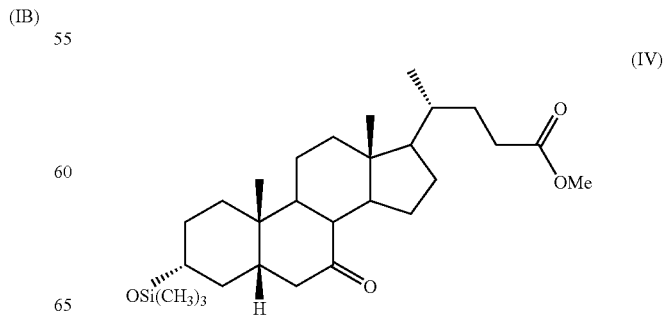

(IV)

c) Silylating methyl 3α-trimethylsiloxy-7-keto-5β-cholanate (IV) obtained in stage (b) with trimethylchlorosilane in the presence of a strong base to obtain methyl 3α-,7α-di-trimethylsiloxy-6-en-5β-cholanate (V),

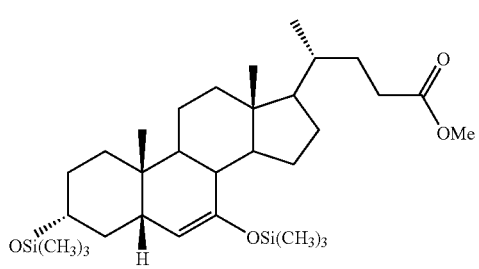

(V)

d) Reacting methyl 3α-,7α-di-trimethylsiloxy-6-en-5β-cholanate (V) with the aldehyde R—CHO in which R has the meanings indicated above and a Lewis acid, to obtain methyl 3α-hydroxy-6-alkylidene-7-keto-5β-cholanate (VI),

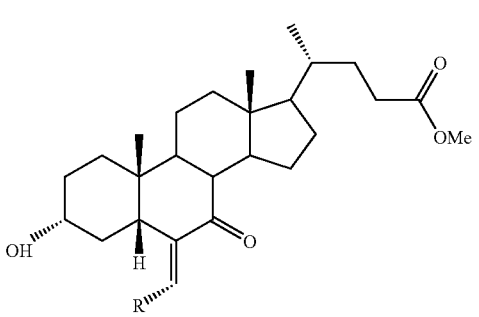

(VI)

e) hydrolysis of methyl 3α-hydroxy-6-alkylidene-7-keto-5β-cholanate to 3α-hydroxy-6-alkylidene-7-keto-5β-colanic acid (VII),

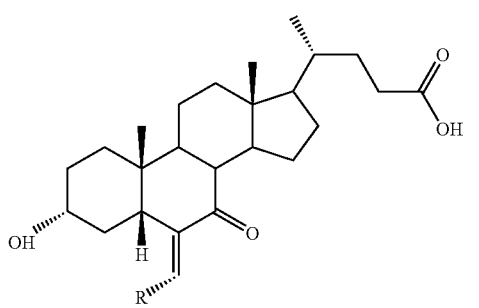

(VII)

f) hydrogenating 3α-hydroxy-6-alkylidene-7-keto-5β-cholanic in an aqueous alkaline environment with Pd/C to 3α-hydroxy-6β-alkyl-7-keto-5β-cholanic acid

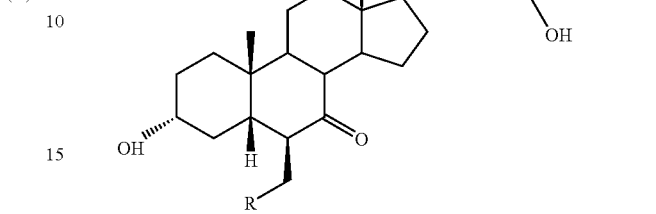

(VIII)

g) optionally heat treating the intermediate (VIII) in an aqueous alkaline environment to obtain the corresponding 3α-hydroxy-6α-alkyl-7-keto-5β-cholanic (IX)

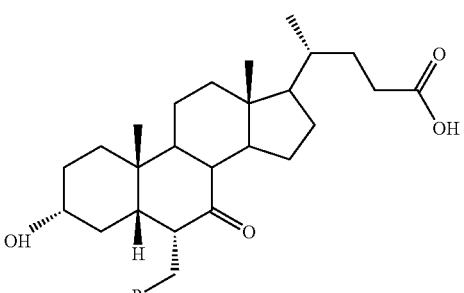

(IX)

h) reducing the ketonic group in position (7) to 7-hydroxy group of the intermediate (VIII) or (IX) according to one of the following alternative operating conditions:
h') reducing 3α-hydroxy-6α-alkyl-7-keto-5β-cholanic compound (IX) with metallic hydride to 3α-,7α-di-hydroxy-6α-alkyl-5β-cholanic acid (IA),
h'') reducing 3α-hydroxy-6α-alkyl-7-keto-5β-cholanic compound (IX) in the presence of sodium and alcohol and obtaining 3α-,7β-di-hydroxy-6α-alkyl-5β-colanic (IC);
h''') reducing 3α-hydroxy-6β-alkyl-7-keto-5β-cholanic (VIII) in the presence of a metallic hydride to 3α-,7α-di-hydroxy-6β-alkyl-5β-cholanic (IB).

The process according to the present invention in particular for obtaining 3α-,7α-di-hydroxy-6α-alkyl-5β-cholanic acids (IA) presents considerable advantages with respect to the known process described above. In fact, although it contemplates a larger number of stages, it allows the product with formula (I) to be obtained with decidedly satisfactory global yields (24.6%), in any case decidedly higher than those of the known process. Moreover, the intermediates do not need to be purified by chromatography and the use of reagents, such as the highly toxic hexamethylenphosphonamide is avoided.

Lastly, with the process of the present invention and as shown above, it is possible to obtain the new compounds of formula (IB) and (IC) which may be used a hepatoprotectors in particular for the treatment and prevention of hepatic diseases of cholestatic origin.

The present invention therefore concerns pharmaceutical compositions containing as active principle at least one of the acids (I-B) and (I-C) and the respective pharmaceutically acceptable salts in combination with suitable excipients and/or diluents.

DETAILED DESCRIPTION OF THE INVENTION

The esterifying reaction of the 3α-hydroxy-7-keto-5β-cholanic acid (II) in stage (a) of the process of the present invention is preferably carried out at a temperature between 30 and 60° C. in an acid environment, in which the acid is preferably methanesulphonic acid.

The silylating reaction of the hydroxy group in position 3α- of methyl 3α-hydroxy-7-keto-5β-cholanate contemplated in stage (b) of the process of the present invention is preferably carried out in an apolar solvent, more preferably an aromatic solvent, even more preferably toluene, in the presence of a hydrogen ion acceptor preferably consisting of a tertiary amine, of aliphatic, alicyclic or heteroaromatic type, even more preferably said tertiary amine is triethylamine.

According to a particularly preferred embodiment, before being used in stage (c), methyl 3-α-trimethylsiloxy-7-keto-5β-cholanate is not isolated and purified, but on the contrary in this stage the oily residue is used which is obtained after evaporating the reaction solvent from which the salts have previously been removed by water extraction.

The subsequent silylation of the ketonic group in position 7 contemplated in stage (c) of the process of the present invention is preferably carried out using as the strong base an alkaline amide obtained from ammonia or an alkaline amide of a secondary aliphatic amine. According to a particularly preferred solution, lithium diisopropylamide is used as the strong base. This reaction is preferably carried out in a polar aprotic solvent, and even more preferably said solvent is tetrahydrofuran.

According to a preferred embodiment the product obtained in stage (c), before being used in the following stage (d), is not isolated and purified, but on the contrary in this case too the oily residue is used obtained by evaporating the reaction solvent from which the salts have been previously extracted with water.

Stage (d) is preferably carried out in an apolar solvent, preferably chosen from alkyl halide, and even more preferably this solvent is methylene chloride.

Stage (d) is preferably carried out using boron trifluoride etherate as the Lewis acid at a temperature between −90 and −60° C. for a period of 2 to 4 hours in the presence of the aldehyde R—CHO in which R has the desired meanings.

Subsequently, the reaction mixture is reacted at a temperature between 0 and 35° C. for a period of 1 to 6 hours.

In this case too, before being used in the following stage (e), the product obtained in stage (d) is not isolated and purified, but the oily residue is used which was obtained after evaporating the reaction solvent, from which the salts and water-soluble components have been removed with water extraction.

Stage (e) is preferably carried out in an alcoholic solvent, preferably methanol, in the presence of an alkaline hydroxide, even more preferably said alkaline hydroxide is an aqueous solution of 30% sodium hydroxide.

The temperature is preferably comprised between 20 and 60° C.

Stage (e) reaction product is preferably isolated after acidification, by crystallisation with an organic solvent, preferably chosen from ethyl acetate and acetone, possibly in the presence of water.

The hydrogenation reaction contemplated in stage (f) is preferably carried out in an aqueous environment in the presence of an aqueous solution of sodium hydroxide with pressure between 1 and 3 atmospheres. When the process of the present invention contemplates stage (g), in particular when the compounds with general formula (IA) or (IC) have to be prepared, this stage is preferably carried out directly on the reaction mixture coming from hydrogenation reaction and is preferably carried by heating said reaction at a temperature between 95 and 105° C. for a few hours to allow the epimerization of the 6-β-ethyl group into 6-α-ethyl.

The reaction product coming from stage (f) or possible stage (g) is isolated from the reaction mixture preferably using the following operating conditions.
1) adding the aqueous solution, from which the catalyst has been removed by filtration is acidified preferably with 85% phosphoric acid,
2) ethyl acetate is added to the mixture obtained in stage (1) and the whole is heated at a temperature between 40 and 70° C.
3) this is then cooled to a temperature between 0 and 30° C. and the precipitate obtained is filtered and subsequently dried.

When the reduction of stage (h) is carried out according to the operative conditions contemplated in stage (h') to obtain the compound with formula (IA) or according to the operative conditions contemplated in stage (h''') to obtain the compound with formula (IB) of the process of the present invention, the metallic hydride is preferably sodium borohydride and the reduction reaction is carried out in an alkaline aqueous solution. The reaction is preferably carried out at a temperature between 70 and 105° C. for 1 hour.

Instead, when the reduction of stage (h) is carried out according to the operating conditions contemplated in stage (h''') it is preferably carried out in linear or branched $C_1$-$C_5$ alcohol, even more preferably in sec-butyl alcohol, at the solvent reflux temperature. The product obtained from stage (h') or (h''') is preferably isolated according to the following operative conditions:
1') adding a water immiscible solvent to the reaction mixture, preferably an apolar solvent such as methylene chloride, and acidifying the mixture preferably with phosphoric acid,
2') stirring and allowing to rest to the mixture obtained thereafter eliminating the aqueous phase,
3') extracting the product from the organic phase with water and ammonia,
4') adding phosphoric acid to the aqueous phase thus obtained and stirring the whole for a few hours at a temperature between 20 and 50° C.,
5') recovering and drying the precipitated product by filtration.

The process of the present invention is suitable in particular for the preparation of compounds with formula (I) in which R is preferably methyl.

Some examples of preparation according to the process of the invention of the compounds with formula (I) and in particular (IA), (IB) and (IC) in cui R=methyl are given for illustrative purposes, but not limitative.

Example 1

Process for Preparing 3α-,7α-dihydroxy-6α-ethyl-5β-cholanic Acid of Formula (IA) in which R=methyl a) Preparation of Methyl 3-α-hydroxy-7-keto-5β-cholanate (III)

17.0 kg of 3-α-hydroxy-7-keto-5β-cholanic acid, 68 kg of methanol and 0.17 kg of methansulphonic acid are charged into a reactor. The reaction mixture is then heated to 30-60° C. for 1 hour and 25.5 kg of demineralised water are added. The mixture obtained is then stirred, cooled to 20-25° C. until a good precipitation is obtained, then cooled further to 0-15° C.

The precipitate is filtered and washed with a mixture of water and methanol and further dried in a oven at about 40° C. 15 kg of methyl 3α-hydroxy-7-keto-5β-cholanate (III) is thus obtained. Stoichiometric yield 85.2%.

b) Preparation of Methyl 3α-trimethylsiloxy-7-keto-5β-cholanate (IV)

15.0 kg of methyl 3α-hydroxy-7-keto-5β-cholanate, 45 kg of toluene, 7.5 kg of triethylamine, 7.5 kg of trimethylchlorosilane are charged into a reactor. The mixture is heated to 70-80° C. and is kept under stirring at that temperature for about 1 hour, then 37.5 kg of water are added and the mixture is stirred at 15-20° C. The lower aqueous phase is then separated and eliminated. The organic phase is concentrated until an oily residue is obtained, which 15 kg of tetrahydrofuran are added to.

The solution thus obtained containing methyl 3α-trimethylsiloxy-7-keto-5β-cholanate (IV) is used in the following stage (c).

c) preparation of methyl 3α-,7α-di-trimethylsililoxy-5β-cholanate (V)

30 kg of tetrahydrofuran are loaded in a reaction, then the mixture is brought to a temperature between −90° and −60° C., 9.8 kg of 100% lithium diisopropylamide and 9.3 kg of trimethylchlorosilane are added, and the whole solution of tetrahydrofuran prepared in (b) and containing methyl 3-α-trimethylsiloxy-7-keto-5β-cholanate is poured. The mixture is then stirred for about 1 hour at a temperature between −60 and −90° C. for 1 hour. A solution of 4.50 kg of sodium bicarbonate and 60 kg of water is then poured and the mixture is stirred at 0-10° C., and the lower aqueous phase is separated and eliminated. The lower phase is then concentrated until an oily residue is obtained, which 45.0 Kg of methylene chloride- are added to.

The solution of methyl 3α-,7α-di-trimethylsililoxy-5β-cholanate thus obtained is sent to the next stage (d).

d) Preparation of Methyl 3α-hydroxy-6-ethyliden-7-keto-5β-cholanate (VI) in which R=Methyl The whole solution of methyl 3α,7-α-di-trimethylsililoxy-5β-cholanate in methylene chloride coming from the preceding example in charged into a reactor and cooled to −90/−60° C. 1.97 kg of acetaldehyde and 5.5 kg of boron trifluoride etherate are then added. The reaction mixture is kept under stirring at the above temperature for 2/4 hours. After that it is heated to 30-35° C. and kept at that temperature for about 2/4 hours. Then 60 kg of water are added. The mixture obtained is stirred and the aqueous phase is separated. The solution thus obtained containing methyl 3α-hydroxy-6-ethyliden-7-keto-5β-cholanate is sent to the next stage.

e) Preparation of 3α-hydroxy-6-ethyliden-7-keto-5β-cholanic (VII) Acid in which R═CH$_3$ The solution of methyl 3-α-hydroxy-6-ethyliden-7-keto-5β-cholanate in methylene chloride obtained in the previous stage is charged into a reactor. The solvent is then removed by distillation until an oily residue is obtained, which 15 kg of methanol are added to.

The reaction mixture is then heated to 45-50° C. and 7.5 kg of 30% sodium hydroxide are poured, and the reaction mixture is kept at the above temperature for about 1 hour. Then 30 kg of water are added. 45.0 kg of methylene chloride and 7.5 kg of 85% phosphoric acid are subsequently added. The lower organic phase is separated and the aqueous phase is eliminated subsequently. The solvent is removed from the organic phase by distillation until a pasty residue is obtained. About 37.5 kg of ethyl acetate are added to the residue and the mixture is heated to 65-75° C., then cooled to 10-35° C. The precipitate obtained, filtered and washed with ethyl acetate, is dried.

8.0 kg of 3-α-hydroxy-6-ethyliden-7-keto-5β-cholanic acid are obtained, with a stoichiometric yield of 51.8% calculated on methyl 3-α-hydroxy-7-keto-5β-cholanate.

f) preparation of 3-α-hydroxy-6-β-ethyl-7-keto-5β-cholanic acid (IX) in which R═CH$_3$)

8.0 kg of 3-α-hydroxy-6-α-ethyliden-7-keto-5β-cholanic acid, 48.0 kg of water, 5.1 kg of 30% sodium hydroxide, 0.80 kg of 5% Palladium/Carbon are charged into a reactor. The reaction mixture is hydrogenated at a pressure between 1 and 3 atmospheres, until the hydrogen absorption is no longer noted.

(g) preparation of 3α-hydroxy-6-α-ethyl-7-keto-5β-cholanic acid (IX)

At the end of the reaction the mixture is heated to 95-105° C. and is kept at that temperature for a few hours to allow the 3α-hydroxy-6-β-ethyl-7-keto-5β-cholanic acid (VIII) to convert into the corresponding epimer of the desired 3α-hydroxy-6-α-ethyl-7-keto-5β-cholanic acid (IX).

The suspension is filtered, and the catalyst is recovered. 5.1 kg of 85% phosphoric acid 9.6 kg of ethyl acetate are added to the filtered solution, and the reaction mixture is heated to a temperature between 40 and 70° C. It is cooled to a temperature between 0 and 30° C. and the precipitate is recovered by filtration. After washing with ethyl acetate, the precipitate is dried in a oven at 65° C. 5.0 kg of 3α-hydroxy-6α-ethyl-7-keto-β-cholanic acid are obtained. Stoichiometric yield: 62.2%.

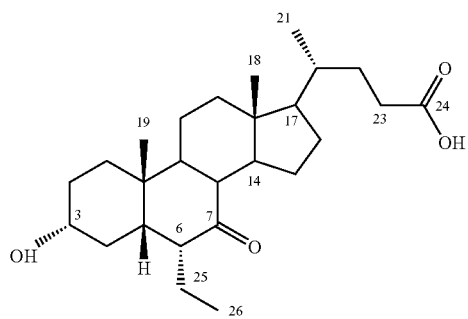

Analysis

3-α-hydroxy-6-α-ethyl-7-keto-5β-cholanic (IX)

C$_{26}$H$_{42}$O$_4$ m.p. 185-188° C.

The $^1$H-NMR analysis carried out with the instrument Bruker DRX-ADVANCE-400 Mhz, dissolving the specimen in CD$_3$OD, gave the following results:

0.62 ppm (s, 3H of methyl C$_{18}$); 0.76 ppm, J=7.4 Hz (t, 3H of methyl C$_{26}$); 0.89 ppm J=6.5 Hz, (d, 3H, of methyl C$_{21}$); 1.18 ppm (s, 3H, of methyl C$_{19}$), 2.21 ppm (m, 2H, —CH$_2$— of C$_{23}$); 2.50 ppm, J=11.17 Hz (ψt, CH on C$_8$); 2.85 ppm J=13 Hz and J=5.4 Hz (dd 1H in C$_6$), 3.50 ppm (m, CH on C$_3$).

The $^{13}$C NMR analysis carried out with the instrument Bruker DRX-ADVANCE-200 Mhz, dissolving the specimen to be analysed in a mixture of $CD_3OD$ and $CDCl_3$, gave the following results:

212.82 ppm ($C_7$); 179.44 ppm ($C_{24}$), 71.26 ppm ($C_3$), 54.77 ppm ($C_{17}$), 51.98 ppm ($C_{14}$), 18.84 ppm ($C_{21}$), 18.34 ppm ($C_{26}$), 12.09 ppm ($C_{18}$).

h') preparation of 3α,7α-dihydroxy-6α-ethyl-5β-cholanic acid with Formula (I) in which R=methyl 5.0 kg of 3α-hydroxy-6α-ethyl-7-keto-β-cholanic acid, 5.0 kg of water, 2.50 kg of sodium hydroxide are loaded in a reactor. The mixture is then heated to 70-105° C. and a mixture of sodium borohydride dissolved in 2.50 kg of water is poured, the mixture is then kept warm for 1 hour, cooled to room temperature, and 10.0 kg of demineralised water, 15.0 kg of methylene chloride and 3.00 kg of 85% phosphoric acid are added. The mixture is stirred, the lower organic phase is separated and the aqueous phase is removed.

Crystallization of the crude product is obtained by cooling the organic solution. This product is dissolved in 50 kg of demineralised water and 1.10 kg of 30% ammonia. The mixture is then stirred until a complete solution is obtained, and keeping the mixture at 20-50° C., 1.50 kg of phosphoric acid is poured. The precipitated mixture is stirred, always at a temperature between 20 and 50° C., then the precipitate is recovered by filtration, washed with water and dried.

4.50 kg of 3α-,7α-di-hydroxy-6α-ethyl-5β-cholanic acid of formula (I) are obtained, in which R=methyl. Stoichiometric yield: 89.6%.

Example 2

Preparation of 3-α,7α-di-hydroxy-6β-ethyl-5β-cholanic acid of Formula (IB) in which R=methyl The 3-α-hydroxy-6β-ethyl-7keto-5β-cholanic acid of formula (VIII) prepared as described in example 1 stages (a)-(f) and isolated as described in stage (g), is reduced using the same operating conditions described in example 1 stage (h'). 3-α,7α-di-hydroxy-6β-ethyl-5β-cholanic acid of formula (IB) is then obtained in which R=methyl.
Analysis

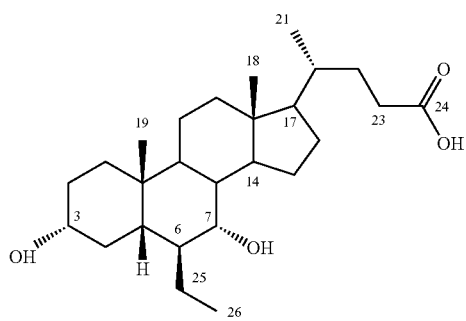

3-α,7-α-di-hydroxy-6-β-ethyl-5β-cholanic (IB)

$C_{26}H_{44}O_4$ m.p. 115-118° C.

The $^1$H-NMR analysis carried out with the instrument Bruker DRX-ADVANCE-400 MHz, dissolving the specimen in $CD_3OD$, gave the following results:

0.70 ppm (s, 3H of methyl $C_{18}$); 0.95 ppm (s, 3H, of methyl $C_{19}$), 1.00 ppm, J=7.65 Hz (t, 3H of methyl $C_{26}$); 1.45 ppm J=3.5 Hz, (d, 3H, of methyl $C_{21}$); 2.25 ppm (m, 2H, —$CH_2$— of $C_{23}$); 3.40 ppm (m, CH on $C_3$), 3.62 ppm (m, CH on $C_7$).

The $^{13}$C NMR analysis carried out with the instrument Bruker DRX-ADVANCE-200 Mhz, dissolving the specimen to be analysed in a mixture of $CD_3OD$ and $CDCl_3$, gave the following results:

177.91 ppm ($C_{24}$), 72.18 ppm ($C_3$), 71.68 ppm ($C_7$); 55.79 ppm ($C_{17}$), 50.83 ppm ($C_{14}$), 18.17 ppm ($C_{21}$), 14 ppm ($C_{26}$), 11.60 ppm ($C_{18}$).

Example 3

Preparation of 3-α,7β-di-hydroxy-6α-ethyl-5β-cholanic acid with Formula (IC) in which R=methyl According to the operative conditions described in example 1 stages (a)-(g), the intermediate (IX) is prepared, to which is added until complete solution sec-butyl alcohol in which sodium has previously been dissolved in molar quantities with respect to the compound (IX) between 3:1 and 3:2. 3-α,7β-di-hydroxy-6α-ethyl-5β-cholanic acid with formula (IC) is obtained in which R=methyl
Analysis 3-α,7-β-di-hydroxy-6-α-ethyl-5β-cholanic (IC)

$C_{26}H_{44}O_4$ m.p. 217-219° C.

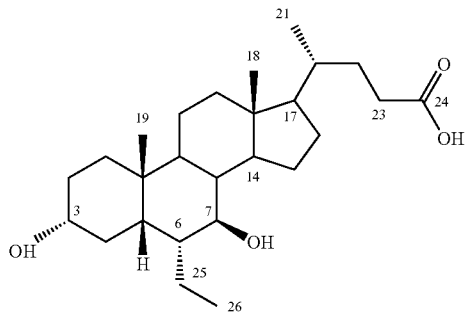

The $^1$H-NMR analysis carried out with the instrument Bruker DRX-ADVANCE-400 MHz, dissolving the specimen in $CD_3OD$, gave the following results:

0.56 ppm (s, 3H of methyl $C_{18}$); 0.73 ppm, J=7.4 Hz (t, 3H of methyl $C_{26}$); 0.81 ppm (s, 3H, of methyl $C_{19}$), 0.82 ppm J=4.60 Hz, (d, 3H, of methyl $C_{21}$); 2.21 ppm (m, 2H, —$CH_2$— of $C_{23}$), 3.80 ppm (br, O—H of hydroxyl on $C_3$, on $C_7$ and of carboxyl $C_{24}$); 3.10 ppm (m, CH on $C_7$); 3.44 ppm (m, CH on $C_3$).

The $^{13}$C NMR analysis carried out with the instrument Bruker DRX-ADVANCE-200 MHz, dissolving the specimen to be analysed in a mixture of $CD_3OD$ and $CDCl_3$, gave the following results:

179 ppm ($C_{24}$), 75.65 ppm ($C_7$), 71.87 ppm ($C_3$), 56 ppm ($C_{17}$), 55 ppm ($C_{14}$), 18.4 ppm ($C_{21}$), 12.24 ppm ($C_{26}$), 11.20 ppm ($C_{18}$).

The invention claimed is:
1. A process for preparing 3α,7α(β)-dihydroxy-6α(β)-alkyl-5β-cholanic acids with general formula (I)

(I)

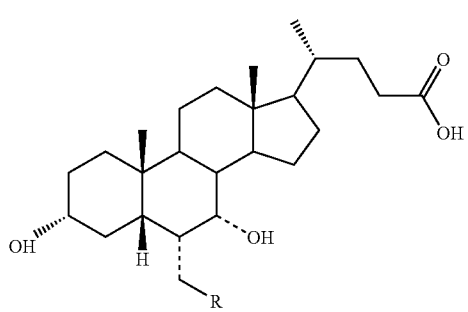

wherein the dashed bond (—) in position 6 and 7 indicates that the substituent may be in position α or β, chosen in the class consisting of:

i) 3α,7α-dihydroxy-6α-alkyl-5β-cholanic acid with general formula (IA)

(IA)

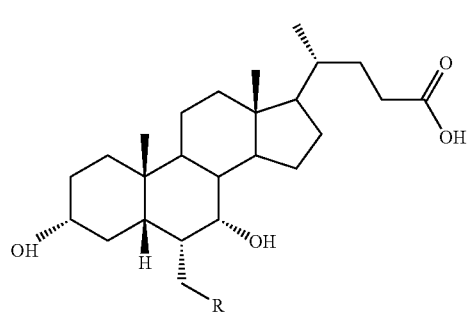

ii) 3α,7α-dihydroxy-6β-alkyl-5β-cholanic acid with general formula (IB)

(IB)

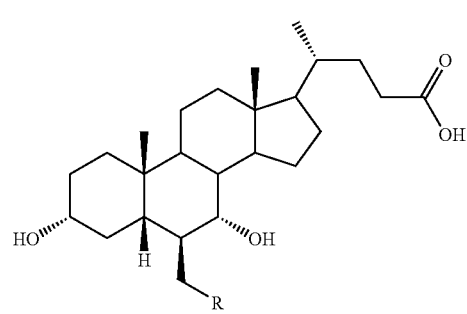

iii) 3α,7β-dihydroxy-6α-alkyl-5β-cholanic acid with general formula (IC)

(IC)

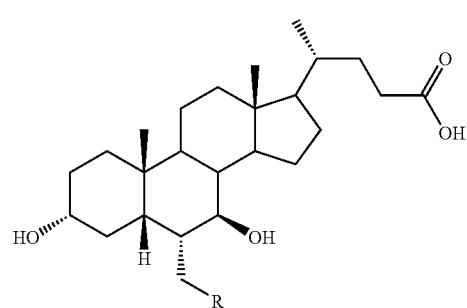

wherein R is a linear or branched $C_1$-$C_5$ alkyl, wherein said process comprises:

a) esterifying 3α-hydroxy-7-keto-5β-cholanic acid (II)

(II)

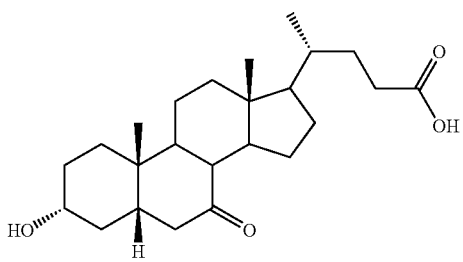

in methanol in an acidic environment to obtain methyl 3α-hydroxy-7-keto-5β-cholanate (III), (III)

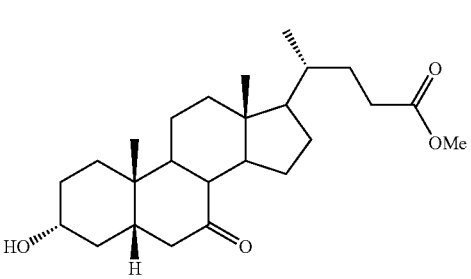

b) silylating methyl 3α-hydroxy-7-keto-5β-cholanate (III) with trimethylchlorosilane to obtain the corresponding methyl 3α-trimethylsiloxy-7-keto-5β-cholanate (IV), (IV)

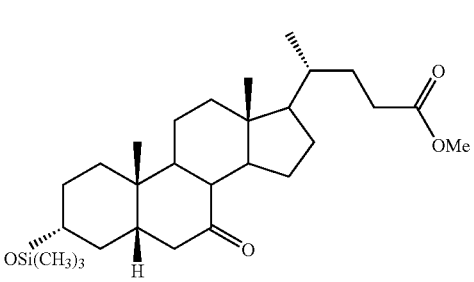

c) silylating methyl 3α-trimethylsiloxy-7-keto-5β-cholanate (IV) in the presence of a strong base and trimethylchlorosilane to obtain methyl 3α,7-di-trimethylsiloxy-6-en-5β-cholanate (V), (V)

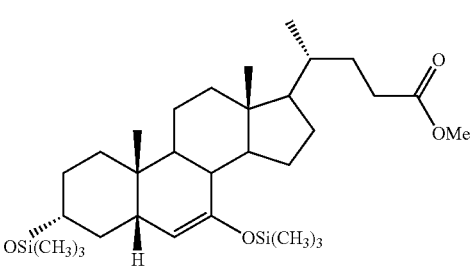

d) reacting methyl 3α,7-di-trimethylsiloxy-6-en-5β-cholanate (V) with the aldehyde R—CHO and a Lewis acid, wherein R is a linear or branched $C_1$-$C_5$ alkyl, to obtain methyl 3α-hydroxy-6-alkylidene-7-keto-5β-cholanate (VI),

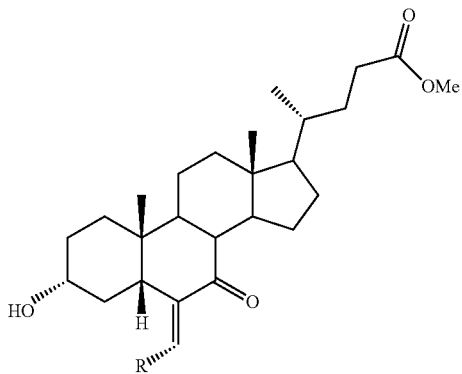

(VI)

e) hydrolysing methyl 3α-hydroxy-6-alkylidene-7-keto-5β-cholanate (VI) to 3α-hydroxy-6-alkylidene-7-keto-5β-cholanic acid (VII),

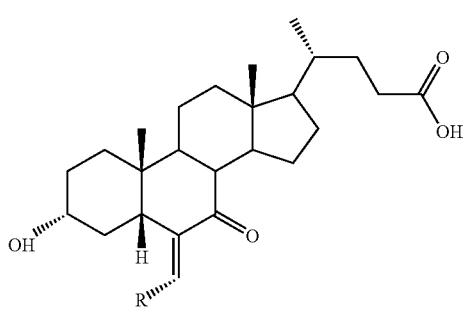

(VII)

f) hydrogenating 3α-hydroxy-6-alkylidene-7-keto-5β-cholanic acid (VII) in an aqueous alkaline environment with Pd/C to 3α-hydroxy-6β-alkyl-7-keto-5β-cholanic acid (VIII)

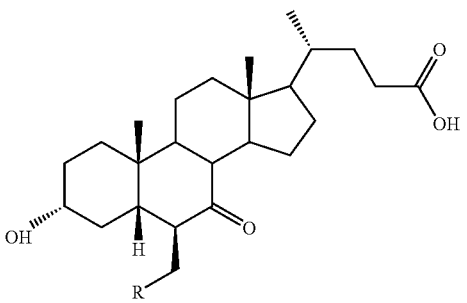

(VIII)

g) optionally heat treating the intermediate (VIII) in an aqueous alkaline environment to obtain the corresponding 3α-hydroxy-6α-alkyl-7-keto-5β-cholanic acid (IX).

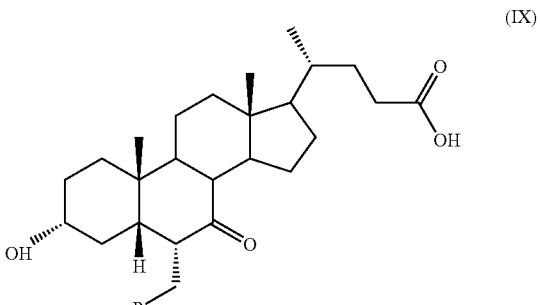

(IX)

h) reducing the ketonic group in position (7) to 7-hydroxy group of the intermediate (VIII) or (IX) according to one of the following alternative operating conditions:
   h') reducing 3α-hydroxy-6α-alkyl-7-keto-5β-cholanic acid (IX) with metallic hydride to obtain 3α,7α-dihydroxy-6α-alkyl-5β-cholanic acid (IA),
   h'') reducing 3α-hydroxy-6α-alkyl-7-keto-5β-cholanic acid (IX) with metallic sodium and alcohol to obtain 3α,7β-dihydroxy-6α-alkyl-5β-cholanic acid (IC);
   h''') reducing 3α-hydroxy-6β-alkyl-7-keto-5β-cholanic acid (VIII) with metallic hydride to obtain 3α,7α-dihydroxy-6β-alkyl-5β-cholanic acid (IB).

2. The process according to claim 1, wherein the esterification of stage (a) is carried out at a temperature between 30 and 60° C. in an acid environment.

3. The process according to claim 2, wherein said acid is methanesulphonic acid.

4. The process according to claim 1, wherein the silylation in stage (b) is carried out in an apolar solvent in the presence of a hydrogen ion acceptor.

5. The process according to claim 4, wherein said apolar solvent is an aromatic solvent.

6. The process according to claim 5 wherein said aromatic solvent is toluene.

7. The process according to claim 4, wherein said hydrogen ion acceptor is a tertiary amine of an aliphatic, alicyclic or heteroaromatic type.

8. The process according to claim 7, wherein said tertiary amine is triethylamine.

9. The process according to claim 1, wherein methyl 3α-trimethylsiloxy-7-keto-5β-cholanate (IV) obtained from stage (b) is not isolated and purified before being used in stage (c).

10. The process according to claim 9, wherein in stage (c), methyl 3α-trimethylsiloxy-7-keto-5β-cholanate (IV) is used as an oily residue which is obtained after evaporating the reaction solvent from which the salts have previously been removed by extraction with water.

11. The process according to claim 1, wherein the subsequent silylation of the ketonic group in stage (c) is carried out using as the strong base an alkaline amide obtained from ammonia or an alkaline amide obtained from a secondary amine.

12. The process according to claim 11, wherein said alkaline amide is lithium diisopropylamide.

13. The process according to claim 1, wherein said stage (c) is carried out in a polar aprotic solvent.

14. The process according to claim 13, wherein said polar aprotic solvent is tetrahydrofuran.

15. The process according to claim 1, wherein methyl 3α,7α-di-trimethylsiloxy-6-en-5β-cholanate (V) obtained in stage (c) is not isolated and purified before being used in stage (d).

16. The process according to claim 15, wherein in stage (d), methyl 3α,7-di-trimethylsiloxy-6-en-5β-cholanate (V) is used as an oily residue which is obtained after evaporating the reaction solvent from which the salts have previously been removed by extraction with water.

17. The process according to claim 1, wherein stage (d) is carried out in an apolar solvent.

18. The process according to claim 17, wherein said apolar solvent is an alkyl halide.

19. The process according to claim 18, wherein said solvent is methylene chloride.

20. The process according to claim 1, wherein the Lewis acid in stage (d) is boron trifluoride etherate.

21. The process according to claim 20 wherein stage (d) is carried out according to the following operating conditions: the reaction mixture is cooled to a temperature between −90° C. −60° C. and for a period of 2 to 4 hours, then the reaction mixture is kept at a temperature between 0 and 35° C. for a period of 1 to 6 hours.

22. The process according to claim 1, wherein methyl 3α-hydroxy-6-alkylidene-7-keto-5β-cholanate (VI) obtained in stage (d), is not isolated and purified before being used in the following stage (e).

23. The process according to claim 22, wherein the hydrolysis in stage (e) is carried out using methyl 3α-hydroxy-6-alkylidene-7-keto-5β-cholanate (VI) as an oily residue obtained after evaporating the reaction solvent from which the salts and water-soluble components have been removed by extraction with water.

24. The process according to claim 1, wherein the hydrolysis reaction in stage (e) is carried out in an alcoholic solvent, in the presence of an aqueous solution of an alkaline hydroxide.

25. The process according to claim 24, wherein said reaction is carried out at a temperature between 20 and 60° C.

26. The process according to claim 1, wherein the hydrogenation in stage (f) is carried out in an aqueous environment in the presence of an aqueous solution of sodium hydroxide at a pressure between 1 and 3 atmospheres.

27. The process according to claim 1 comprising stage (g), wherein stage (g) is carried out directly on the mixture of the reaction obtained from stage (f).

28. The process according to claim 27, wherein said stage (g) is carried out at a temperature between 95 and 105° C. for a few hours to allow the epimerization of the 6β-alkyl group into 6α-alkyl.

29. The process according to claim 1, wherein the reaction product obtained from stage (f), when the process does not contemplate stage (g), or from stage (g), is isolated from the reaction mixture according to the following operating conditions:
1) acidifying the aqueous solution from which the catalyst has been removed by filtration,
2) adding ethyl acetate to the mixture obtained in stage (1) and heating the whole to a temperature between 40 and 70° C., and
3) cooling to a temperature between 0 and 30° C., filtering and drying the precipitate obtained.

30. The process according to claim 1, wherein when the reduction of stage (h) is carried out according to the operating conditions contemplated in stage (h') or according to the operating conditions (h'''), wherein the metallic hydride is sodium borohydride in an aqueous solution in which an alkaline hydroxide has been dissolved.

31. The process according to claim 30, wherein said alkaline hydroxide consists of a solution of 30% sodium hydroxide.

32. The process according to claim 30, wherein the reaction is carried out at a temperature between 70 and 105° C. for 1 hour.

33. The process according to claim 30, wherein the product obtained is isolated according to the following operating conditions:
1') adding a water immiscible solvent to the reaction mixture and acidifying the mixture with phosphoric acid,
2') stirring and allowing to rest the mixture obtained and eliminating the aqueous phase,
3') extracting the product from the organic phase with water and ammonia,
4') adding phosphoric acid to the aqueous phase thus obtained and stirring the whole at a temperature between 20 and 50° C., and
5') recovering and drying the precipitated product by filtration.

34. The process according to claim 1 comprising stage (h'), wherein the reduction reaction is carried out in a linear or branched alcohol $C_1$-$C_5$ at the solvent reflux temperature.

35. The process according to claim 34, wherein said alcohol is sec-butyl alcohol.

36. The process according to claim 1 wherein R is methyl.

37. The process according to claim 1 for preparing 3α,7α-dihydroxy-6α-ethyl-5β-cholanic acid.

38. 3α-hydroxy-6β-alkyl-7-keto-5β-cholanic acid (VIII)

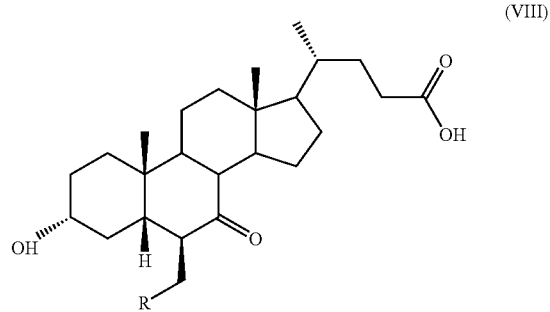

wherein R is a linear or branched $C_1$-$C_5$ alkyl.

39. 3α-hydroxy-6α-alkyl-7-keto-5β-cholanic acid (IX)

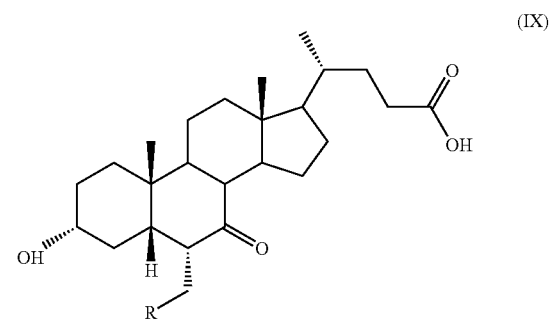

wherein R is a linear or branched $C_1$-$C_5$ alkyl.

* * * * *

UNITED STATES PATENT AND TRADEMARK OFFICE
CERTIFICATE OF CORRECTION

| | | |
|---|---|---|
| PATENT NO. | : 7,994,352 B2 | Page 1 of 1 |
| APPLICATION NO. | : 11/914559 | |
| DATED | : August 9, 2011 | |
| INVENTOR(S) | : Massimo Ferrari et al. | |

It is certified that error appears in the above-identified patent and that said Letters Patent is hereby corrected as shown below:

On the title page, item (54) and col. 1, line 1, the title "PROCESS FOR PREPARING 3A(β)-7A(β)-DIHYDROXY-6A(β)-ALKYL-5β-CHOLANIC ACID" should read --PROCESS FOR PREPARING 3α(β)-7α(β)-DIHYDROXY-6α(β)-ALKYL-5β-CHOLANIC ACID--.
On the cover, page 2 under the section Foreign Patent Documents, the text "WO-200400752 A2" should read --WO-2004007521 A2--.
Column 13, line 14, the term "(—)" should read --(----)--.
Column 16, line 29, column 17, lines 17-18, 44 and 56-57; and column 18, lines 5 and 18, at each occurrence, the term "C." should read --C--.
Column 16, line 65, the text "3α,7α-di-trimethylsiloxy-6-en-5β-cholanate" should read --3α,7-di-trimethylsiloxy-6-en-5β-cholanate--.
Column 18, line 21, the text "stage (h')" should read --stage (h")--.

Signed and Sealed this
Eighth Day of November, 2011

David J. Kappos
*Director of the United States Patent and Trademark Office*